United States Patent [19]
Walter et al.

[11] Patent Number: 4,734,173
[45] Date of Patent: Mar. 29, 1988

[54] METHOD AND APPARATUS FOR THE MANUFACTURE OF DENTAL PROTHESES

[75] Inventors: Herbert Walter, Flourn-Winzeln; Erich Körber, Tübingen; Josef Gentischer, Remshalden, all of Fed. Rep. of Germany

[73] Assignee: Herbert Walter, Fed. Rep. of Germany

[21] Appl. No.: 940,840

[22] Filed: Dec. 12, 1986

[30] Foreign Application Priority Data

Dec. 13, 1985 [DE] Fed. Rep. of Germany ....... 3544123

[51] Int. Cl.⁴ .................. B23H 7/22; B23H 7/30; B23H 9/12
[52] U.S. Cl. ................ 204/129.1; 204/224 M; 204/225; 204/129.55; 219/69 E; 219/69 M
[58] Field of Search ........... 204/129.5, 129.55, 224 M, 204/225, 129.1; 219/69 E, 69 M

[56] References Cited

U.S. PATENT DOCUMENTS

| | | | |
|---|---|---|---|
| 3,356,598 | 12/1967 | Cabau | 204/129.5 X |
| 3,393,141 | 7/1968 | Trenn et al. | 204/129.5 X |
| 3,689,729 | 9/1972 | Neward et al. | 204/129.1 X |
| 3,694,610 | 9/1972 | Saito et al. | 219/69 E X |
| 3,723,695 | 3/1973 | Gutnajer | 204/129.1 X |
| 4,363,627 | 12/1982 | Windeler | 219/69 M X |
| 4,627,136 | 12/1986 | Kreylos et al. | 219/69 M X |

FOREIGN PATENT DOCUMENTS

3320902 3/1985 Fed. Rep. of Germany.

Primary Examiner—Donald R. Valentine
Attorney, Agent, or Firm—Jones, Tullar & Cooper

[57] ABSTRACT

The present invention relates to a method and an apparatus for the manufacture of dental prostheses by means of an electroerosion process by using two template electrodes for erosive excavation. The dental prosthesis to be inserted is made directly from solid material which has not been previously worked. The negative templates of the dental prosthesis contained in the template electrodes can also be made by the electroerosion method. The manufacture of the dental prosthesis can be accomplished by a simultaneous movement of the two template electrodes or by manufacture of the two form halves of the dental prosthesis at different times.

8 Claims, 3 Drawing Figures

METHOD AND APPARATUS FOR THE MANUFACTURE OF DENTAL PROTHESES

FIELD OF THE INVENTION

The present invention relates to a method and an apparatus for the manufacture of dental protheses by means of an electroerosion process, and in particular to such a method and apparatus according to which the dental prosthesis is worked on with the use of template electrodes for erosive excavation, wherein a model of the dental prosthesis is formed and negative impressions thereof are produced.

BACKGROUND OF THE INVENTION

Such a method and apparatus are know per se. A method for producing dental prostheses is known from German laid open application DE-OS No. 31 18 890, in which a metallic secondary part is anchored removably by means of fastening elements on an also metallic fixed primary part. Bars or friction pins serve as fastening elements, for which corresponding receivers with exact seating are provided in the primary and secondary parts. An erosion machine is used by means of which the seats for the bar in the primary as well as in the secondary parts are produced together by electroerosion. The erosion machine is used only as a drilling tool for producing the seats for the bars. How the primary part is fitted to the tooth stump or the secondary part is fitted to the primary part in regard to the contact surfaces, however, remains completely open.

Further, a method for the production of dental prostheses is known from German laid open application DE-OS No. 33 20 902, wherein a plaster model stump, made electrically conductive and coated and corresponding to the tooth stump formed by the dentist, is utilized as an electrode for the electroerosive finishing of the snug fit of a dental prosthesis made by castings. Until a cementable model of the dental prosthesis made by casting can be produced, five negative-positive transfers are required. The first casting step consists of the making of a negative cast of the natural tooth stump. From this cast a positive plaster model is made. The positive plaster model is supplemented by a wax model made by the dental technician. The positive wax model is embedded in a mold in a secondary cast material and fused. Metal is poured into the casting thus formed and a metal model of the dental prosthesis made in this way.

Each of these casting steps contains errors inherent in the process which partially appear as positive, partially as negative dimensional changes. These dimensional changes are caused, for example, by changes in the volume caused by polymerization of the impression material when making the negative cast. During the production of the plaster model expansion may occur. The processing defects in the wax are the result of the properties of the wax and the working temperature of the wax. The cooling of the wax and setting processes in the embedding material, too, may lead to errors. The working temperature of the liquid cast metal and its change in dimensions during cooling also adversely effect the forming of the metallic model, for example, pores and bubbles are formed and furthermore, structural changes occur which lead to corrosion. The process-related errors add up with each cast leading to considerable dimensional changes which no longer can be accepted and result in considerable finishing work to achieve a snug fit, wherein the cost of this finishing work can amount to as much as half of the total cost of the dental prosthesis.

Another considerable disadvantage of a dental prosthesis made by casting is that only castable materials can be used or that castable materials cannot be used because of a too high melting temperature. For example, work hardened materials could not be used, which are considerably more cost-effective and which exclude from the start the formation of bubbles and structural changes.

SUMMARY OF THE INVENTION

It is therefore an object of the present invention to produce technically uncomplicated dental prostheses at favorable cost, to make possible their manufacture without the need for finishing to achieve a snug fit, and without the material problems arising during casting and thereby to use new and better materials which cannot be used in casting.

The special advantages of the invention are the avoidance of the casting process during manufacture of the dental prosthesis. Because of the electroerosive shaping of the dental prosthesis directly from the solid material, all fitting errors between the dental prosthesis and the prepared tooth stump are avoided. If electrically conductive material is used from the start for the making of the negative impression of the tooth and if this is also done when making the model of the dental prosthesis, the negative forms of the template electrodes for the erosive process can be produced directly from those electrically conductive elements. Because of the absence of a casting step when making the dental prosthesis, cost-effective materials can be used which are, for example, work hardened. These materials have, in part, better properties than gold in their use as dental prostheses.

The invention is further described below by means of exemplary embodiments and the drawings.

DESCRIPTION OF THE PREFERRED EMBODIMENTS

Figure 1:
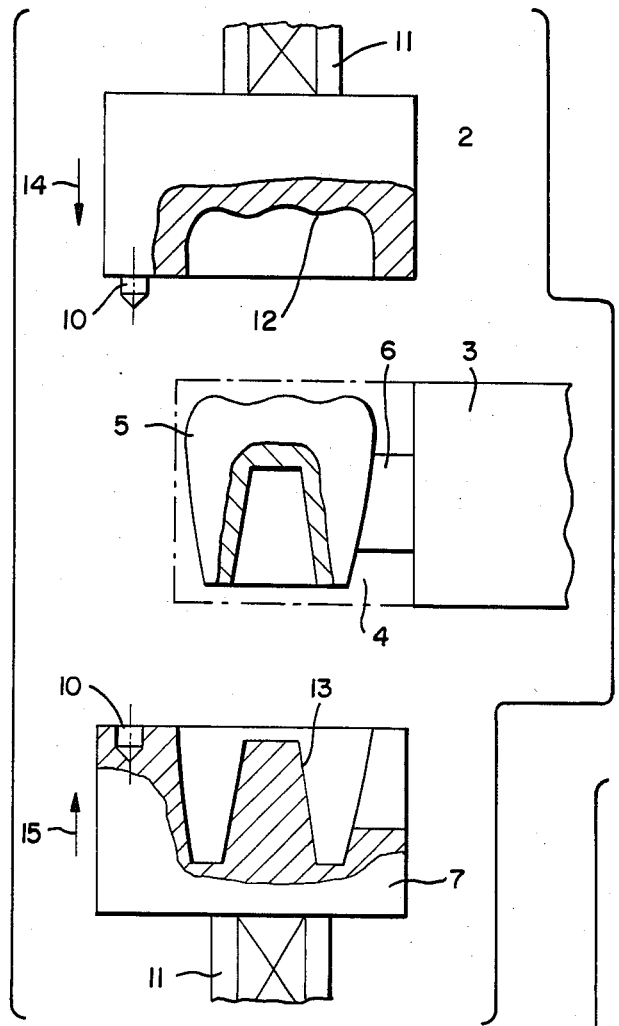
FIG. 1 is a schematic view of a first embodiment of the apparatus for the manufacture of dental prostheses by means of electroerosion according to the present invention.

FIG. 1 shows an apparatus for the manufacture of a dental prosthesis 5 from solid material 3. The solid material is that material from which the dental prosthesis to be inserted is to be made. This can be, for example, work-hardened materials such as (INCONELL) or any other material usable for a dental prosthesis. The dental prosthesis 5 is produced by means of two template electrodes 2 and 7, which are also designated as upper and lower template electrodes. These electrodes are connected to an electroerosion apparatus not further shown for reasons of simplification and which is constructed according to the state of the art. The two template electrodes 2 and 7 are formed as upper and lower half shells and have on their inside surfaces negative templates 12 and 13, respectively, which have an electrically conductive surface and are based on the model of the dental prosthesis or the impression of the tooth stump. The template electrodes 2 and 7 have positioning elements 11 for positioning the two electrodes and, furthermore, a positioning element 10, in the form of a pin and groove, which assures the exact fit of the two template electrodes with respect to one another.

The negative template electrodes 2 and 7 for the dental prosthesis 5 can also be made in the erosive manner directly from solid material not previously worked. The negative templates 12 and 13 of the template electrodes can be manufactured by two different methods. On the one hand, the upper template electrode 2 can be made from a model of the dental prosthesis 5, wherein the material for the manufacture of the model is electrically conductive from the start. On the other hand, the lower template electrode 7 can be made from a negative impression of the tooth stump, wherein the material for the making of the negative impression consists of electrically conductive material from the start.

Another method for the manufacture of the negative templates 12 and 13 of the template electrodes 2 and 7 consists of the template electrodes originally being made of a basic material which is not electrically conductive, the surface of which is later made electrically conductive for the negative templates 12 and 13, which, for example can be done by means of the application of colloidal silver on the non-conductive material and the subsequent electrolytic deposition of a metal layer.

As casting material for the template electrodes, made from the start of electrically conductive material, metal, conductive plastic or graphite are considered, for example.

Figure 2:
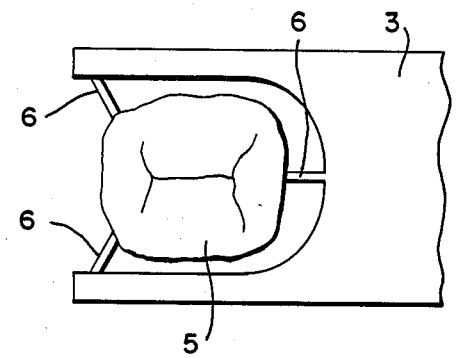
FIG. 2 is a top view of the prosthesis attached to the material from which it is formed by the apparatus of FIG. 1.

It can further be seen from FIGS. 1 and 2 that the templates of the upper and lower template electrodes 2 and 7 are formed in such a way that during the erosion process thin connecting bridges 6 remain between the forming dental prosthesis 5 and the remainder of the solid material 3. These connecting bridges 6 serve to anchor the dental prosthesis 5 during the working process and are created by a special design of the electrodes 2 and 7. The bridges 6 are broken off after the erosion process, the breaks are smoothed, wherein these bridges were from the start disposed at non-critical places of the dental prosthesis.

The method of manufacture of the dental prosthesis 5 from solid material 3 in accordance with FIG. 1 is achieved as follows. The two template electrodes 2 and 7 with their negative templates 12 and 13 are moved together facing each other onto the solid material 3 at the same time, as indicated by the two arrows 14 and 15.

The dental prosthesis 5 thus is formed by the simultaneous bringing together of the template electrodes 2 and 7.

Figure 3:
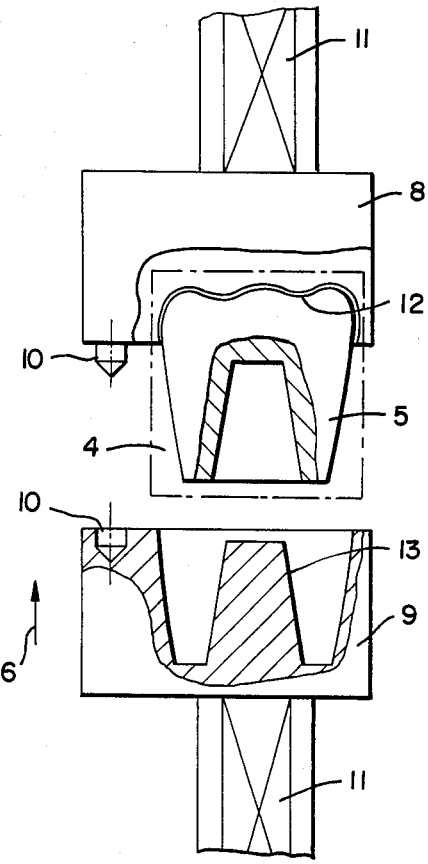
FIG. 3 is a schematic view of a second embodiment for the manufacture of a dental prosthesis without casting by means of electroerosion according the the present invention.

Another method for the manufacture of the dental prosthesis 5 is described in FIG. 3. Shown there are also an upper and a lower template electrode 8 and 9, formed identically with the template electrodes 2 and 7 according to the exemplary embodiment of FIG. 1, already described. Identical parts are indicated by identical reference numerals and are not described again. This second method for the manufacture of the dental prosthesis 5 is achieved as follows. From the solid material 4 which, for example, could be a metal block, only the first half of the dental prosthesis 5 is erosively shaped by means of the upper template electrode 8; here the crown of the tooth has been shaped as the first part. Of course this sequence can also be reversed and the shaping of the lower part of the dental prosthesis can be started first. After the first half of the dental prosthesis has been started, the already pre-shaped half of the dental prosthesis 5 is connected with the negative template 12 of the template electrode 8 by, for example, glueing. Thereby the not-completed developing dental prosthesis 5 is firmly seated in the template electrode 8. Now the second half of the dental prosthesis 5 is eroded by means of the lower template electrode 9, wherein the template electrode 9 is moved in the direction of the arrow 16 towards the upper template electrode 8 and thereby the dental prosthesis 5. After completion of the dental prosthesis 5, which in this method of production does not have connecting bridges, the dental prosthesis 5 is removed from the negative template of the upper electrode 8. With this, the dental prosthesis 5 is finished, with no finishing work being needed for a snug fit.

What is claimed is:

1. An apparatus for use in the manufacture of dental prostheses from solid material by means of an electroerosion process for working the dental prosthesis, comprising:
    an upper template electrode in the form of a shell having an electrically conductive inner surface shaped as a negative impression of the upper part of the prosthesis;
    a lower template electrode in the form of a shell having an electrically conductive inner surface shaped as a negative impression of the lower part of the prosthesis; and
    means for positioning said upper and lower template electrodes so that when said template electrodes engage, the negative impressions form the outline of the prosthesis.

2. The apparatus as defined in claim 1, wherein the electrically conductive inner surface of both template electrodes are shaped directly from a model of the dental prosthesis which comprises electrically conductive material.

3. The apparatus as defined in claim 1, wherein the electrically conductive inner surface of both template electrodes is applied to a non-conductive base material.

4. The apparatus as defined in claim 1, wherein the inner surfaces of both template electrodes are shaped so that resulting prosthesis includes connecting bridges to the remaining solid material.

5. A method for manufacturing dental prostheses, from solid material by means of an electroerosion process, comprising the steps of:
    preparing a model of the prosthesis, the model having both an outer surface and an inner surface, the inner surface serving to be fitted on a supporting surface of a tooth;
    preparing a first template electrode from the model to include a negative impression of a part of the outer surface of the model;
    preparing a second template electrode from the model to include a negative impression of a part of the inner surface of the model; and
    aligning both template electrodes and using them in an electroerosion process to excavate the prosthesis from a solid metal block, the template electrodes being applied to the metal block from opposite sides, such that at least a part of the outer surface of the prosthesis is formed by the first template electrode, and the inner surface of the prosthesis is formed by the second template electrode, thereby producing the prosthesis from the remaining part of the block between the template electrodes.

6. The method as defined in claim 5, wherein the negative impressions are produced by an electroerosion process applied directly to the respective template electrode as solid material not previously worked.

7. The method as defined in claim 5, wherein the prosthesis is produced simultaneously by the movement of the template electrodes toward each other.

8. The method as defined in claim 5, wherein the prosthesis is produced by:
- first forming a part of the prosthesis by one of the two template electrodes;
- removably attaching the partly formed prosthesis to said one of the two template electrodes; and
- then forming the remainder of the prosthesis by the other of the two template electrodes.

* * * * *